United States Patent
Anstadt

(10) Patent No.: US 12,115,363 B1
(45) Date of Patent: Oct. 15, 2024

(54) SYSTEM AND METHOD FOR INTRODUCING A CONSTRUCT EITHER ON OR AROUND THE SURFACE OF THE HEART

(71) Applicant: Lifebridge Technologies, LLC, Dayton, OH (US)

(72) Inventor: Mark P. Anstadt, Kettering, OH (US)

(73) Assignee: Lifebridge Technologies LLC, Dayton, OH (US)

( * ) Notice: Subject to any disclaimer, the term of this patent is extended or adjusted under 35 U.S.C. 154(b) by 0 days.

(21) Appl. No.: 18/447,786

(22) Filed: Aug. 10, 2023

(51) Int. Cl.
*A61M 60/569* (2021.01)
*A61M 60/191* (2021.01)
*A61M 60/289* (2021.01)
*A61M 60/865* (2021.01)
*A61M 29/02* (2006.01)

(52) U.S. Cl.
CPC ........ *A61M 60/865* (2021.01); *A61M 60/191* (2021.01); *A61M 60/289* (2021.01); *A61M 2029/025* (2013.01); *A61M 2205/702* (2013.01)

(58) Field of Classification Search
CPC .............. A61M 60/865; A61M 60/191; A61M 60/289; A61M 2029/025; A61M 2205/702
USPC .......................................................... 600/16
See application file for complete search history.

(56) References Cited

U.S. PATENT DOCUMENTS

| | | |
|---|---|---|
| 2,826,193 A | 3/1958 | Vineberg |
| 2,889,780 A | 6/1959 | Binford |
| 3,053,249 A | 9/1962 | Smith |
| 3,233,607 A | 2/1966 | Bolle |
| 3,279,464 A | 10/1966 | Kline |
| 3,304,501 A | 2/1967 | Ruthenberg |
| 3,371,662 A | 3/1968 | Heid |
| 3,376,863 A | 4/1968 | Kolobow |
| 3,449,767 A | 6/1969 | Bolie |
| 3,455,298 A | 7/1969 | Anstadt |
| 3,478,737 A | 11/1969 | Rassman |
| 3,513,836 A | 5/1970 | Sausse |
| 3,587,567 A | 6/1971 | Schiff |
| 3,590,815 A | 7/1971 | Schiff |
| 3,613,672 A | 10/1971 | Schiff |
| 3,674,381 A | 7/1972 | Schiff |
| 4,048,990 A | 9/1977 | Goetz |
| 4,192,293 A | 3/1980 | Asrican |
| 4,281,669 A | 8/1981 | MacGregor |
| 4,448,190 A | 5/1984 | Freeman |
| 4,536,893 A | 8/1985 | Parravicini |
| 4,609,176 A | 9/1986 | Powers |

(Continued)

*Primary Examiner* — Erin M Piateski
(74) *Attorney, Agent, or Firm* — LaMorte & Associates P.C.

(57) ABSTRACT

A system and method for evaluating, altering and/or creating an opening around the heart to receive a construct. Using a minimally invasive techniques, a first guide is advanced into an area adjacent to the heart. The first guide is used to probe the area and determine if an opening can be safely formed in that area. The guide is then used to direct a larger guide catheter into the targeted area. The larger guide catheter is used to direct a more robust guide into the targeted area. The robust guide is then used to direct a delivery guide catheter into the targeted area. The delivery guide catheter can be used to stall a device deployment guide. Either the delivery guide catheter or the device deployment guide can be used to advance the construct into the targeted area.

17 Claims, 15 Drawing Sheets

(56) References Cited

U.S. PATENT DOCUMENTS

| | | |
|---|---|---|
| 4,621,617 A | 11/1986 | Sharma |
| 4,662,358 A | 5/1987 | Farrar |
| 4,684,143 A | 8/1987 | Sata |
| 4,957,477 A | 9/1990 | Lundback |
| 4,979,936 A | 12/1990 | Stephenson |
| 5,066,111 A | 11/1991 | Inokuchi |
| 5,089,017 A | 2/1992 | Young |
| 5,098,369 A | 3/1992 | Heilman et al. |
| 5,098,442 A | 3/1992 | Grandjean |
| 5,119,804 A | 6/1992 | Anstadt |
| 5,131,905 A | 7/1992 | Grooters |
| 5,156,154 A | 10/1992 | Valenta, Jr. et al. |
| 5,158,978 A | 10/1992 | Rubin |
| 5,169,381 A | 12/1992 | Snyders |
| 5,199,804 A | 4/1993 | Rimbey et al. |
| 5,205,722 A | 4/1993 | Hammond |
| 5,256,132 A | 10/1993 | Snyders |
| 5,273,518 A | 12/1993 | Lee et al. |
| 5,322,067 A | 6/1994 | Prater |
| 5,330,505 A | 7/1994 | Cohen |
| 5,364,337 A | 11/1994 | Guiraudon et al. |
| 5,368,451 A | 11/1994 | Hammond |
| 5,374,287 A | 12/1994 | Rubin |
| 5,383,840 A | 1/1995 | Heilman et al. |
| 5,385,528 A | 1/1995 | Wilk |
| 5,429,584 A | 7/1995 | Chu |
| 5,476,502 A | 12/1995 | Rubin |
| 5,496,353 A | 3/1996 | Grandjean et al. |
| 5,533,958 A | 7/1996 | Wilk |
| 5,558,617 A | 9/1996 | Heilman et al. |
| 5,562,595 A | 10/1996 | Neisz |
| 5,658,237 A | 8/1997 | Francischelli |
| 5,674,259 A | 10/1997 | Gray |
| 5,697,884 A | 12/1997 | Francischelli et al. |
| 5,697,952 A | 12/1997 | Francischelli et al. |
| 5,707,336 A | 1/1998 | Rubin |
| 5,713,954 A | 2/1998 | Rosenberg et al. |
| 5,716,379 A | 2/1998 | Bourgeios et al. |
| 5,738,627 A | 4/1998 | Kovacs et al. |
| 5,749,839 A | 5/1998 | Kovacs |
| 5,769,800 A | 6/1998 | Gelfand et al. |
| 5,800,334 A | 9/1998 | Wilk |
| 5,861,558 A | 1/1999 | Buhl et al. |
| 5,876,345 A | 3/1999 | Eaton et al. |
| 5,902,229 A | 5/1999 | Tsitlik et al. |
| 5,908,378 A | 6/1999 | Kovacs et al. |
| 5,910,124 A | 6/1999 | Rubin |
| 5,919,209 A | 7/1999 | Schouten |
| 5,971,910 A | 10/1999 | Tsitlik et al. |
| 5,971,911 A | 10/1999 | Wilk |
| 5,980,571 A | 11/1999 | Nomura et al. |
| 6,042,532 A | 3/2000 | Freed et al. |
| 6,044,298 A | 3/2000 | Salo et al. |
| 6,059,750 A | 5/2000 | Fogarty et al. |
| 6,076,013 A | 6/2000 | Brennan et al. |
| 6,095,968 A | 8/2000 | Snyders |
| 6,110,098 A | 8/2000 | Renirie et al. |
| 6,123,726 A | 9/2000 | Mori et al. |
| 6,132,363 A | 10/2000 | Freed et al. |
| 6,183,412 B1 | 2/2001 | Benkowski et al. |
| 6,206,820 B1 | 3/2001 | Kazi et al. |
| 6,238,334 B1 | 5/2001 | Easterbrook, III et al. |
| 6,251,061 B1 | 6/2001 | Hastings et al. |
| 6,254,525 B1 | 7/2001 | Reinhardt et al. |
| 6,282,445 B1 | 8/2001 | Reinhardt et al. |
| 6,298,266 B1 | 10/2001 | Rubin et al. |
| 6,309,380 B1 | 10/2001 | Larson et al. |
| 6,328,689 B1 | 12/2001 | Gonzalez et al. |
| 6,408,205 B1 | 6/2002 | Renirie et al. |
| 6,432,039 B1 | 8/2002 | Wardle |
| 6,438,411 B1 | 8/2002 | Guttman et al. |
| 6,464,655 B1 | 10/2002 | Shahinpoor |
| 6,485,407 B2 | 11/2002 | Alferness et al. |
| 6,508,756 B1 | 1/2003 | Kung et al. |
| 6,540,659 B1 | 4/2003 | Milbocker |
| 6,547,716 B1 | 4/2003 | Milbocker |
| 6,572,534 B1 | 6/2003 | Milbocker et al. |
| 6,602,182 B1 | 8/2003 | Milbocker |
| 6,612,978 B2 | 9/2003 | Lau et al. |
| 6,616,596 B1 | 9/2003 | Milbocker |
| 6,622,045 B2 | 9/2003 | Snell et al. |
| 6,626,821 B1 | 9/2003 | Kung et al. |
| 6,641,604 B1 | 11/2003 | Adelman et al. |
| 6,682,474 B2 | 1/2004 | Lau et al. |
| 6,730,016 B1 | 5/2004 | Cox et al. |
| 6,757,561 B2 | 6/2004 | Rubin et al. |
| 6,808,483 B1 | 10/2004 | Ortiz et al. |
| 6,846,296 B1 | 1/2005 | Milbocker et al. |
| 6,971,127 B2 | 12/2005 | Richards |
| 7,331,221 B2 | 2/2008 | Wise et al. |
| 7,494,459 B2 | 2/2009 | Anstadt et al. |
| 7,871,366 B2 | 1/2011 | Criscione et al. |
| 8,187,160 B2 | 5/2012 | Criscione et al. |
| 8,460,161 B2 | 6/2013 | Saadat et al. |
| 10,463,496 B2 | 11/2019 | Criscione et al. |
| 11,511,102 B2 | 11/2022 | Criscione et al. |
| 2001/0041821 A1* | 11/2001 | Wilk .................. A61M 60/531 600/16 |
| 2003/0032855 A1 | 2/2003 | Shahinpoor |
| 2004/0010180 A1 | 1/2004 | Scorvo |
| 2004/0024315 A1 | 2/2004 | Chalana |
| 2004/0059183 A1 | 3/2004 | Jozef et al. |
| 2004/0078067 A1 | 4/2004 | Thompson et al. |
| 2004/0102674 A1 | 5/2004 | Zadini et al. |
| 2004/0116769 A1 | 6/2004 | Jassawalla |
| 2004/0167375 A1 | 8/2004 | Couvillon |
| 2004/0225177 A1 | 11/2004 | Coleman et al. |
| 2004/0267086 A1 | 12/2004 | Anstadt et al. |
| 2005/0113632 A1 | 5/2005 | Ortiz et al. |
| 2005/0148814 A1 | 7/2005 | Fischi et al. |
| 2005/0234289 A1 | 10/2005 | Anstadt et al. |
| 2006/0106442 A1* | 5/2006 | Richardson .......... A61N 1/0587 607/119 |
| 2006/0142634 A1 | 6/2006 | Anstadt et al. |
| 2006/0167334 A1 | 7/2006 | Anstadt et al. |
| 2006/0211909 A1 | 9/2006 | Anstadt et al. |
| 2007/0197859 A1 | 8/2007 | Schaer et al. |
| 2008/0257412 A1 | 10/2008 | Gordon |
| 2010/0152523 A1 | 6/2010 | MacDonald et al. |
| 2011/0196189 A1 | 8/2011 | Milbocker |
| 2012/0095498 A1 | 4/2012 | Stefanchik et al. |
| 2015/0080640 A1 | 3/2015 | Lillehel |
| 2016/0101230 A1 | 4/2016 | Ochsner |
| 2016/0262889 A1* | 9/2016 | Laham .................. A61F 2/2481 |

\* cited by examiner

SYSTEM AND METHOD FOR INTRODUCING A CONSTRUCT EITHER ON OR AROUND THE SURFACE OF THE HEART

BACKGROUND OF THE INVENTION

1. Field of the Invention

In general, the present invention relates to the systems and methods used to introduce various constructs around the heart so that those constructs can act directly upon the surface of the heart. More particularly, the present invention relates to systems and methods that are used to enter the pericardial space and/or the area around the heart to evaluate and/or safely prepare this space to hold, fit, and achieve desired functionality of a construct in vivo. In this manner, the construct can be properly positioned, can have room to function, and is capable of achieving a desired therapeutic goal while reducing the risk for complications.

2. Prior Art Description

In simple terms, the term "pericardial area" implies the area just outside the heart's surface. Within the pericardial area, the heart is normally surrounded by the pericardium. The pericardium is a double-walled sac that surrounds the heart and the roots of the great vessels that lead from the heart. The pericardium has an outer layer, called the fibrous pericardium, that is primarily made from inelastic connective tissue that is typically referred to as the pericardial sac. Furthermore, the heart's surface has an outer layer, which is made of serous membrane referred to as the epicardium or outer surface of the heart. The space between the pericardial sac and the exterior of the heart is called the pericardial cavity or pericardial space. The pericardial space typically contains pericardial fluid, which protects and lubricates the heart. The pericardial space is generally small and only contains a small amount of fluid to lubricate the heart's surface during normal pump function. The pericardial space can contain fibrous connective tissue or scar tissue that extends between the epicardium of the heart and the pericardial sac. If the heart has been diseased or has been previously operated upon, there is often scar tissue that extends across the pericardial space. In some instances, the pericardial space may be completely absent after surgery or obliterated and/or obstructed by scar tissue.

Accordingly, it can be difficult to create an opening within the pericardial space, if present. Likewise, if there is no pericardial space, or if the space is severely compromised, it can be very difficult to create an opening in the tissue surrounding the heart. However, the entry, verifications, and if needed, creation of such a space around the heart is critical if an artificial construct, such as a heart pump, is to be safely and effectively placed against the heart.

Constructs, such as heart pump devices, are generally designed to fit around, or on, the ventricles of a surgically exposed heart. Accordingly, such constructs are typically applied using open heart surgical techniques. Likewise, creating the required opening within the pericardial space is also often accomplished using open surgical techniques. However, open heart surgeries have many inherent problems. Open heart surgery is highly invasive and can result in significant blood loss and infection risk. Furthermore, open heart surgeries require longer surgical times, longer stays at the hospital, and longer recovery times. Lastly, open heart surgeries often leave visible scars on the chest of the patient.

It is for these and other reasons that many physicians and patients prefer minimally invasive surgical procedures. Minimally invasive heart surgeries involve making small incisions in the chest to reach the heart. The obvious problem is that non-blood contacting heart pumps and like constructs can be too large to use in traditional minimally invasive procedures. The result is that the surgical opening must be enlarged to accommodate the construct being inserted. Consequently, the minimally invasive procedure becomes more invasive than desired. This problem can be addressed by a surgical team in two ways. First, a smaller or partial construct can be used that is small enough to pass through the minimally invasive incision. Alternatively, a collapsible heart pump can be used. Such heart pumps typically have a mesh framework that can be drawn into a thoracoscopic insertion tube and advanced into the body. Once in the body, the mesh framework expands as it is expelled from a thoracoscopic insertion tube. The expanded shape, once released from the thoracoscopic tube, can assume a shape to encircle the heart or act on at least part of the heart. Such prior art devices are exemplified by U.S. Pat. No. 10,463,496 to Criscone and U.S. Pat. No. 11,511,102 to Criscone.

Regardless of what heart pump or other construct is used, the intended space required for applying such a construct must be interrogated and/or prepared before the construct can be safely installed or implanted. If no space is evaluated or prepared, the construct may not be able to enter the space safely or the construct may not fit in the space available. Furthermore, the construct may not have the enough space to function properly and/or it may have too much space causing it to become displaced or dysfunctional after it is implanted or inserted.

In the prior art, verifying and/or creating the proper opening needed for entry of a construct into the pericardial space is a primary obstacle. If a natural opening is not present, then an opening in the pericardial space is typically created in one of two manners. In a first manner, a balloon catheter is inserted into the pericardial space through a small chest incision. Once in the pericardial space, the catheter is inflated to create a larger opening. This works to a limited degree. However, this only addresses the creation of a small opening in the pericardial space. The space created may or may not be optimally positioned or sized to safely accommodate the introduction of a construct around the heart. When the construct is introduced, the construct relies upon the opening that has been previously prepared. Therefore, using a prior art balloon catheter, a significant amount of time and surgical skill would be required in order to create an appropriate opening and prepare and/or interrogate the space needed for the proper placement of a construct.

In an attempt to simplify the surgical procedure, a second method has been developed that relies upon the use of multi-fingered spacing instruments. Such instruments are exemplified by U.S. Pat. No. 8,460,181 to Saadat, and U.S. Patent App. Pub. No. 2012/0095498, to Stefanchik. These instruments advance a plurality of preconfigured fingers into the pericardial space or the tissue surrounding the heart. However, should one of these fingers contact scar tissue or some abnormality, the fingers can easily cause a tear in either the pericardium sac and/or the heart. This is problematic since many people who need pneumatic heart pumps tend to have had earlier heart procedures that created scar tissue or other obstacles around the heart. Accordingly, prior art devices that deploy multiple fingers lack the finesse to safely create an opening for a construct that is properly sized and properly positioned. Once an opening is created, a construct will position itself within the opening. The proper positioning of a construct is critical to both its safety and effectiveness. A poorly positioned construct, due to a poorly formed opening can result in a suboptimal functionality of the construct, or even a life-threatening complication.

A need therefore exists for an improved system and method for evaluating and preparing an opening around the heart. A need also exists for an improved system and method for introducing a heart pump or similar construct into the opening created. These needs are met by the present invention as described and claimed below.

SUMMARY OF THE INVENTION

The present invention is a system and method for evaluating, altering and/or creating an opening around the heart that is properly sized and positioned to receive and retain a construct that acts upon the heart. An opening is prepared in the area near the heart that is to receive the construct. Using minimally invasive techniques, a first guide is advanced into a targeted area adjacent to the heart. The first guide is used to probe the area and determine if an opening of the needed size is present or can be safely formed in that area. The first guide is then used to direct a larger guide catheter into the targeted area. The first guide is removed from within the lumen of the guide catheter. The larger guide catheter is used to direct a more robust second into the targeted area. This process can be repeated until either a guide or a guide catheter of a given size is in place.

Depending on the targeted area's ability to accommodate the intended construct, one or more balloon catheters can be advanced into the targeted area over a guide or through a guide catheter. Such balloon catheters can be expanded within the targeted area to either verify or create space needed to accommodate the intended construct. Once the targeted area is confirmed or created, a construct is advanced into the opening. The construct can be advanced over a guide or through a guide catheter. Once the construct is in positioned within the targeted space, it is still accessible. The construct can therefore be tested in-vivo before withdrawing the guides and/or guide catheters. Alternatively, if the presence of the guides supports the construct and assists in the operation of the construct, then the guides can be left in place.

BRIEF DESCRIPTION OF THE DRAWINGS

For a better understanding of the present invention, reference is made to the following description of exemplary configurations thereof, considered in conjunction with the accompanying drawings, in which.

DETAILED DESCRIPTION OF THE DRAWINGS

Although the present invention system and method can be varied in different ways, only a few embodiments are illustrated. The exemplary embodiments are being shown for the purposes of explanation and description. The exemplary embodiments are selected in order to set forth some of the best modes contemplated for the invention. The illustrated embodiments, however, are merely exemplary and should not be considered limitations when interpreting the scope of the appended claims.

Figure 1:
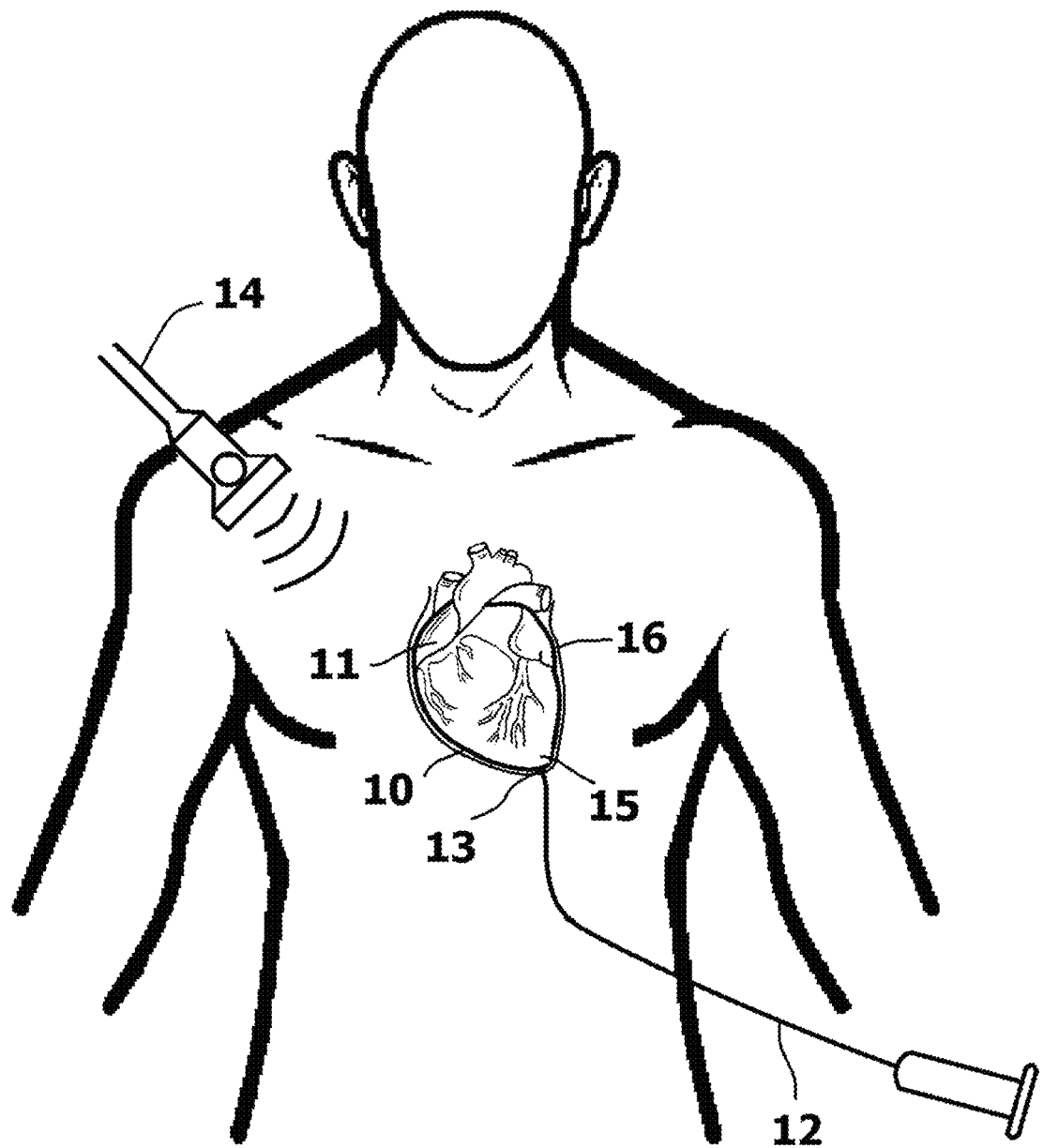
FIG. 1 is a diagram illustrating the insertion of a first, atraumatic, soft, flexible small-bore guide into the pericardial cavity during a minimally intrusive procedure.

Referring to FIG. 1, the pericardial space 10 that typically surrounds the heart 11 is accessed in a minimally invasive procedure. If there is no pericardial space 10, the pericardial area at the interface between the heart 11 and the surrounding tissue is accessed. A soft, flexible, atraumatic, small-bore guide 12 is inserted into the chest. The tip 13 of the small-bore guide 12 is directed toward the heart 11. This can be done blind with experience but is preferably with the assistance of a medical imaging system 14, such as x-ray or ultrasound. The tip 13 of the small-bore guide 12 is directed generally toward the ventricular apex 15 of the heart 11, wherein the small-bore guide 12 is used to enter the pericardial space 10. If no pericardial sac 16 is present, then the small-bore guide 12 is directed toward the interface between the ventricular apex 15 and the surrounding tissue. In this later circumstance, the characteristics of the small-bore guide 12 may need to be altered to allow the small-bore guide 12 to be advanced as to facilitate the intent of creating a path for entry.

Once near the heart's surface 11, the small-bore guide 12 is used to probe and interrogate the pericardial space 10 and/or the tissue in the pericardial area surrounding the heart 11. The small-bore guide 12 is highly flexible and will not be able to pass through scar tissue or other obstructions. As such, by probing various areas around the heart 11, it can be determined if an appropriate opening is naturally available. If not, the probing determines what areas adjacent to the heart 11 are appropriate for the creation of an opening and which areas are not.

Figure 2:
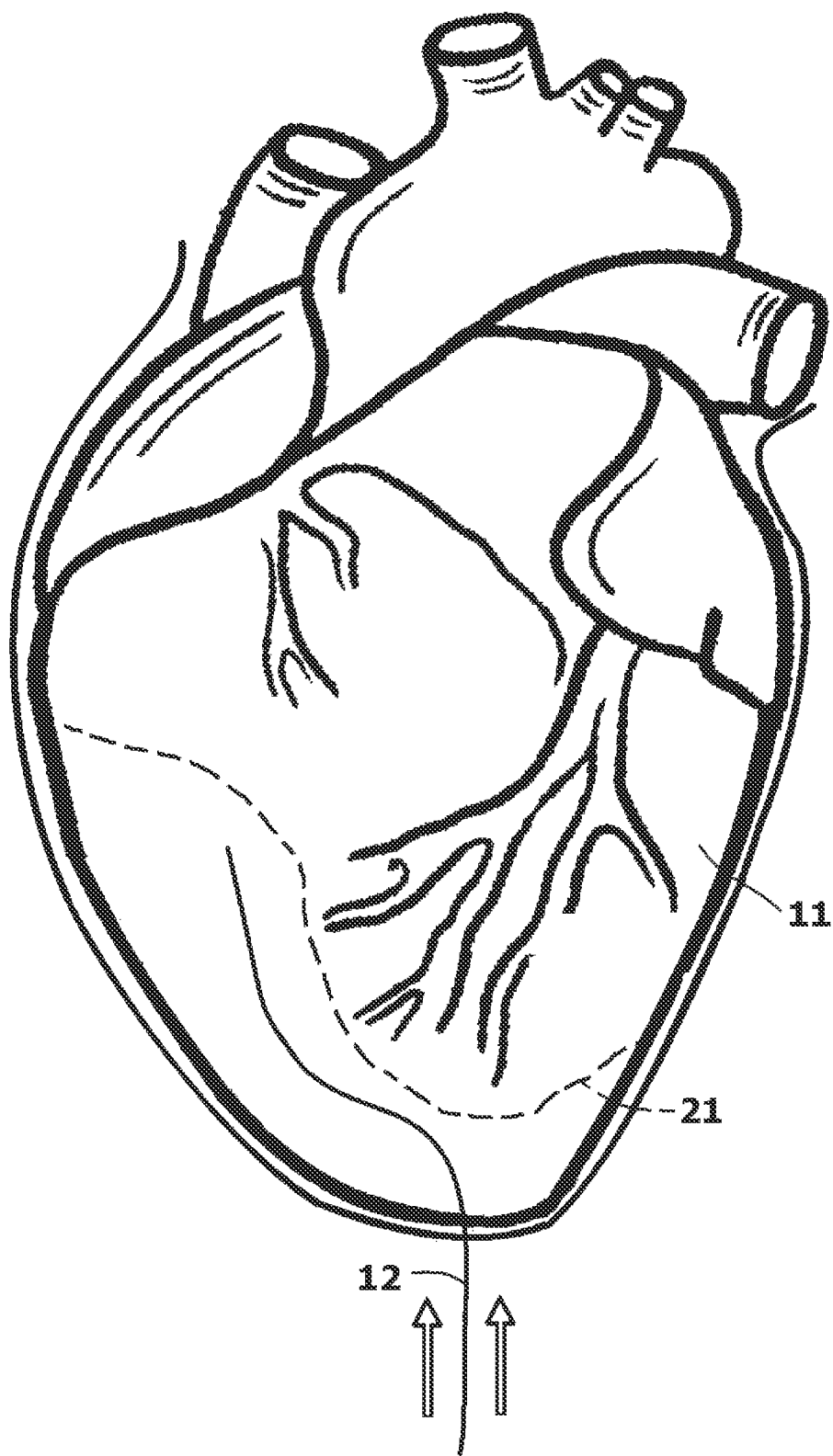
FIG. 2 is a diagram illustrating the positioning of the small-bore guide in a targeted area around the heart.

Referring to FIG. 2 in conjunction with FIG. 1, it will be understood that the initial small-bore guide 12 can be properly positioned near the heart 11 in a targeted area 21 that is to eventually receive a construct. The targeted area 21 can be probed and otherwise interrogated using the small-bore guide 12. However, if the targeted area 21 does not contain a natural opening that is acceptable, then the targeted area 21 must first be prepared for the construct by creating an opening of the right size and orientation to receive the construct.

Figure 3:
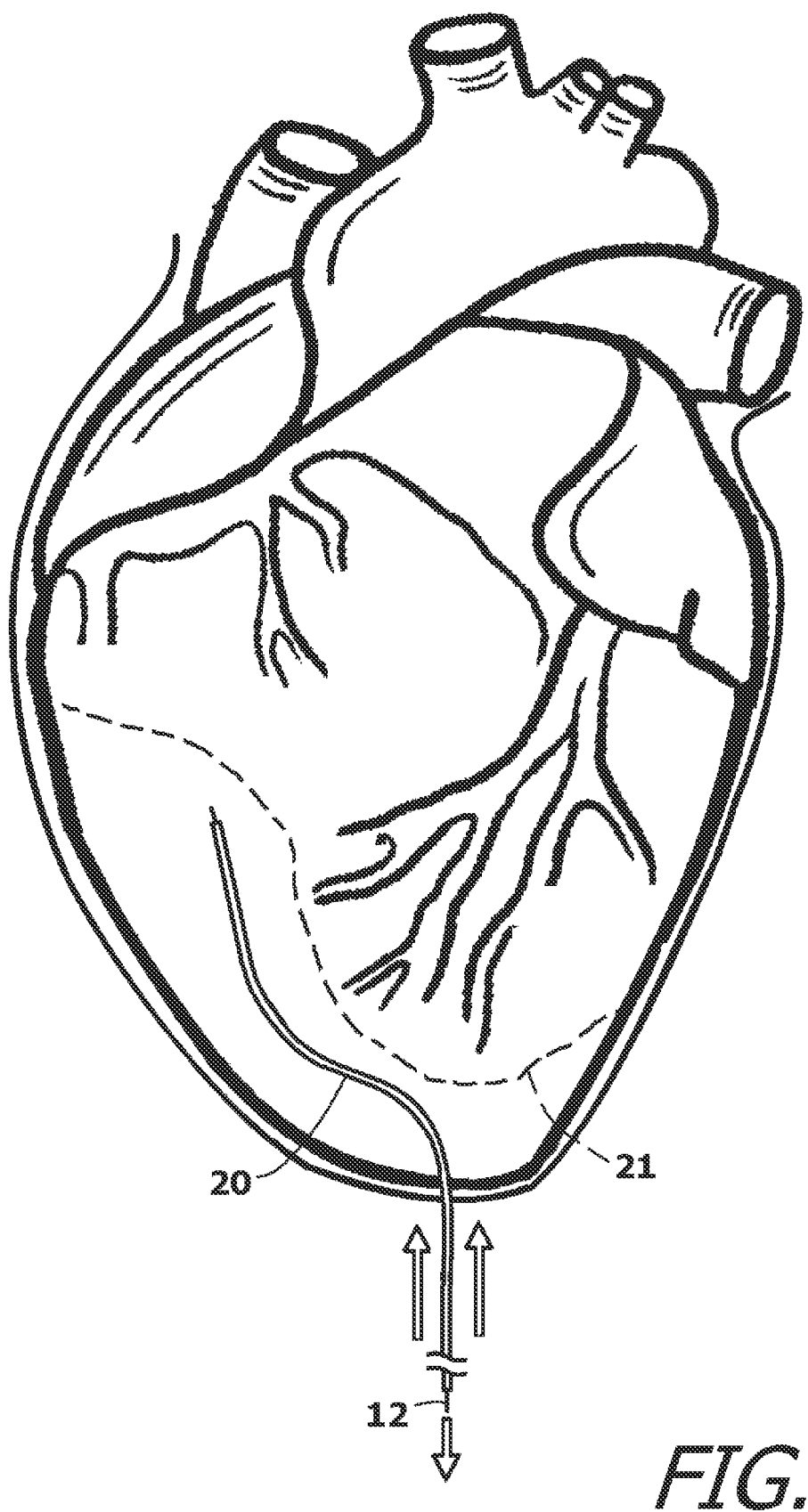
FIG. 3 is a diagram illustrating the insertion of a larger second guide catheter over the first small-bore guide into the targeted area surrounding the heart.

Referring to FIG. 3 in conjunction with FIG. 2, it can be seen that to prepare the targeted area 21, a first guide catheter 20 is advanced along the small-bore guide 12. The larger first guide catheter 20 follows the path of the small-bore guide 12 and ends up in the same position and orientation as the small-bore guide 12. The small-bore guide 12 is then removed from the first guide catheter 20. The open lumen of the first guide catheter 20 therein provides an open pathway into the targeted area 21 that is to prepared for the construct.

Figure 4:
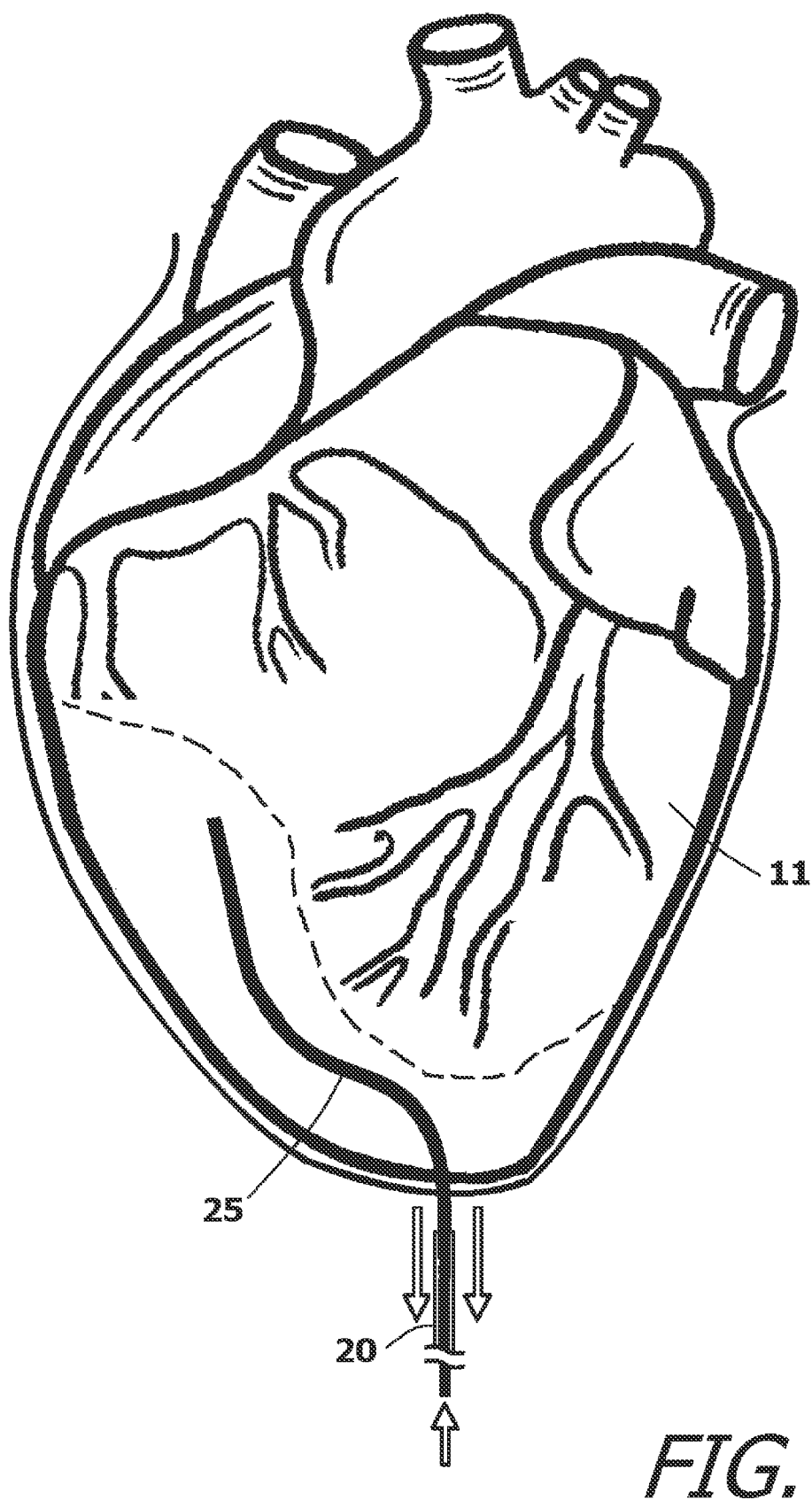
FIG. 4 is a diagram illustrating the insertion of a larger second guide into the second guide catheter and into the targeted area surrounding the heart.

The first guide catheter 20 may be too small for practical use. Referring to FIG. 4 in conjunction with FIG. 3 and FIG. 2, it can be seen that a stiffer second guide 25 is advanced into the lumen of the first guide catheter 20. The second guide 25 follows the first guide catheter 20 and winds up in the same position as was the initial small-bore guide 12. Once the second guide 25 is in place, the first guide catheter 20 can be removed leaving the stiffer second guide 25 in place.

Figure 5:
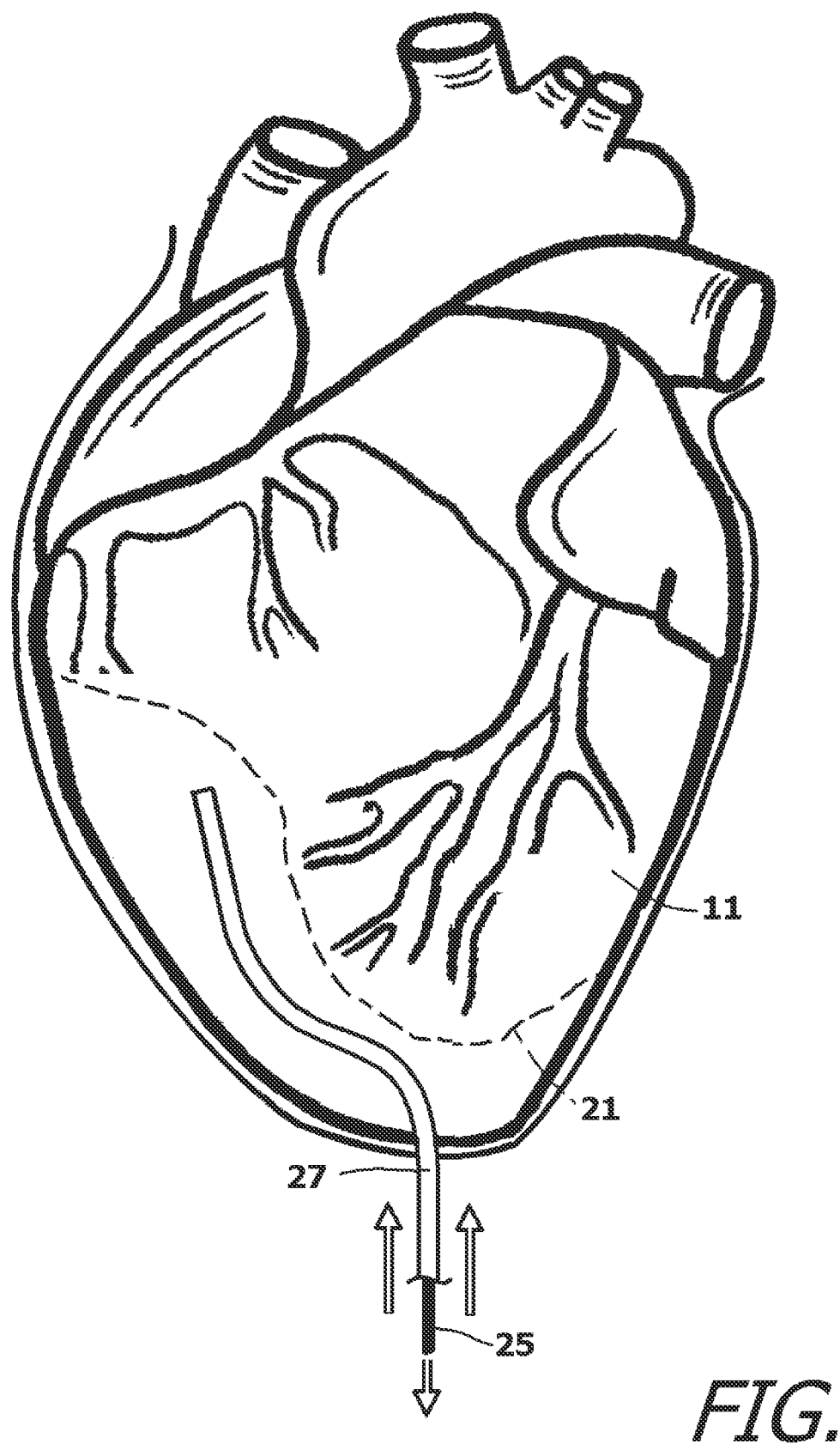
FIG. 5 is a diagram illustrating the insertion of a delivery guide catheter over the second guide and into the targeted area surrounding the heart.

The stiffer second guide 25 has the structural integrity and shape needed to guide a larger bore catheter into the targeted area 21 next to the heart 11. Referring to FIG. 5, it can be seen that a larger bore delivery guide catheter 27 is advanced along the second guide 25. Once the delivery guide catheter 27 is in position at the targeted area 21, the second guide 25 is removed. The process of substituting larger wires and larger catheters can be repeated until a delivery guide catheter of a desired internal diameter is in place in the same orientation and position as was the initial small-bore guide 12 of FIG. 2. The lumen of the delivery guide catheter 27 therein provides a usable open pathway to the targeted area 21 that is to be prepared for the construct.

Figure 6:
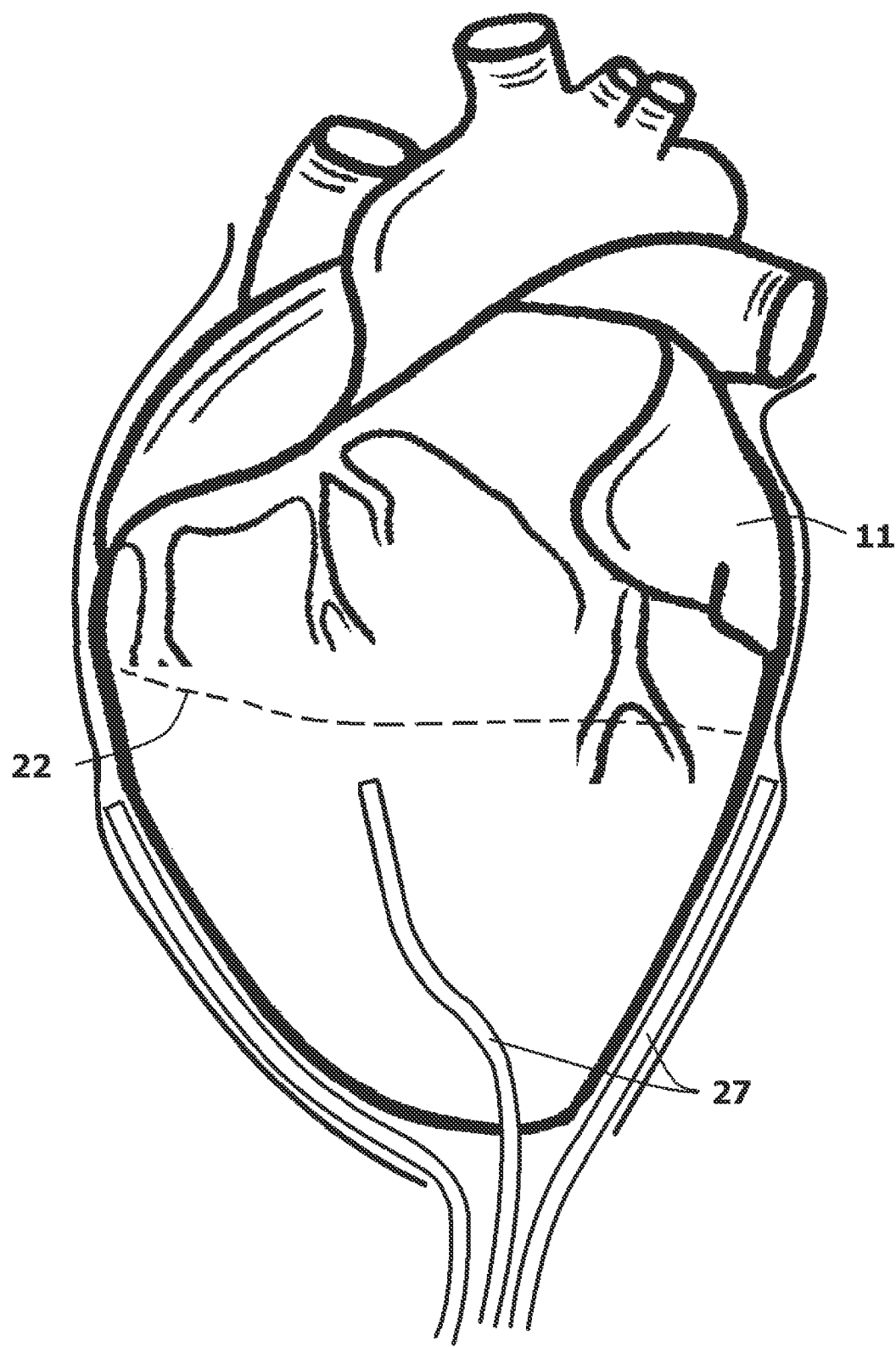
FIG. 6 is a diagram showing the insertion of multiple delivery guide catheters into targeted areas surrounding the heart.
Figure 7:
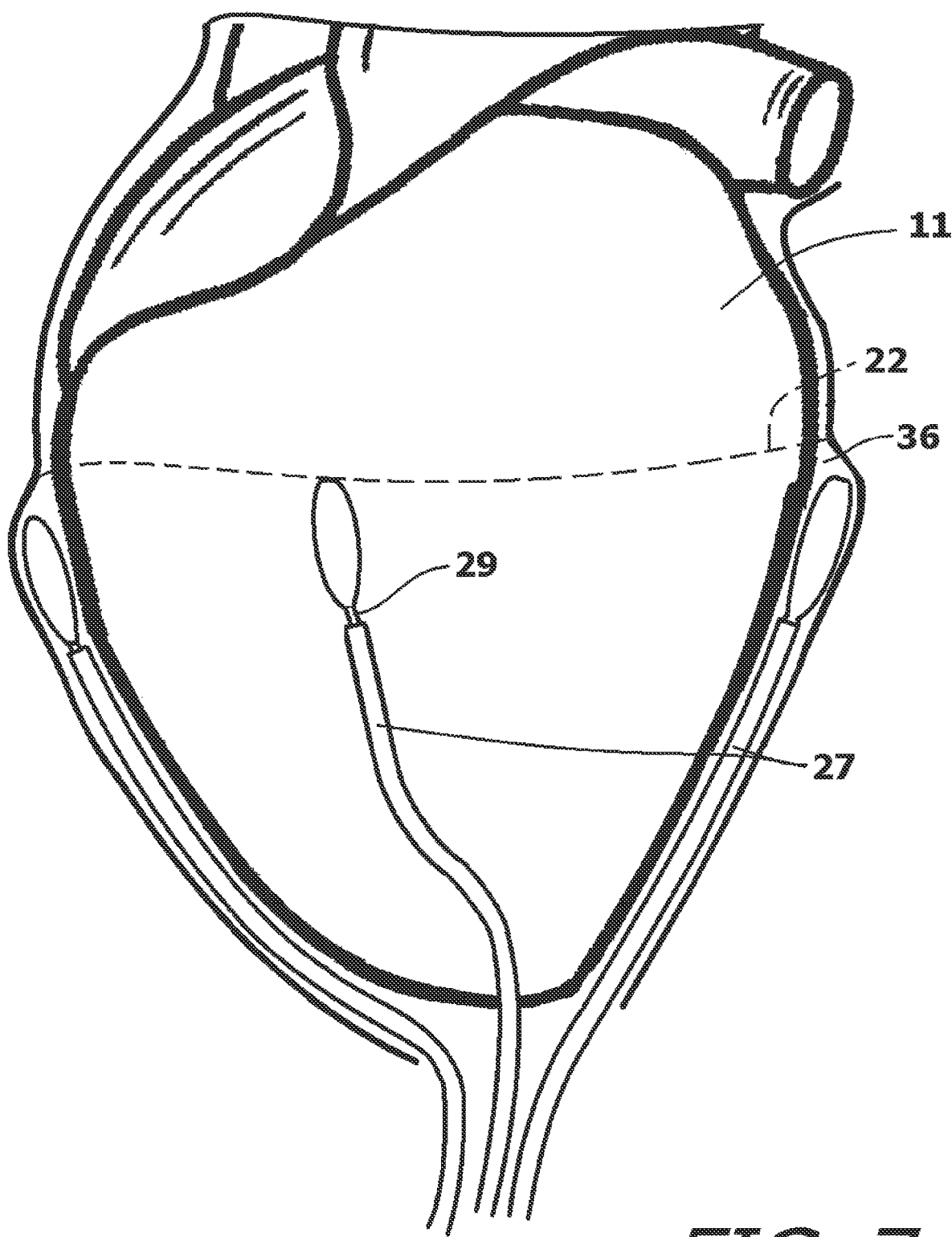
FIG. 7 is a diagram showing the insertion of multiple balloon catheters into a targeted area around the heart.

If an opening needs to be created in the pericardial area, then the delivery guide catheter 27 can be used to introduce the instrumentation needed to create the opening within the targeted area 21. In the previous figures, a single delivery guide catheter 27 is being shown positioned next to the heart 11. It should be understood that the same described technique can also be used to position multiple delivery guide catheters 27 around the heart. Referring to FIG. 6 and FIG. 7, it can be seen that if multiple delivery guide catheters 27 are used, they can be used to channel multiple balloon catheters 29 around the heart 11. One or more balloon catheters 29 are advanced around the heart 11 and are used to create an appropriate opening 36 for a construct. The balloon catheters 29 can be traditional balloon expanders. However, each balloon catheter 29 is preferably a custom catheter of the type described below.

Figure 9:
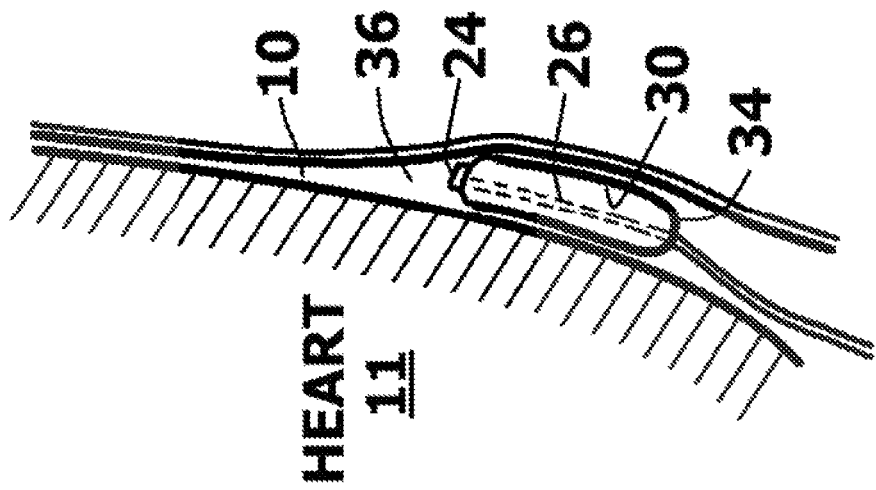
FIG. 9 shows a balloon catheter in the pericardial space in a fully expanded condition.
Figure 8:
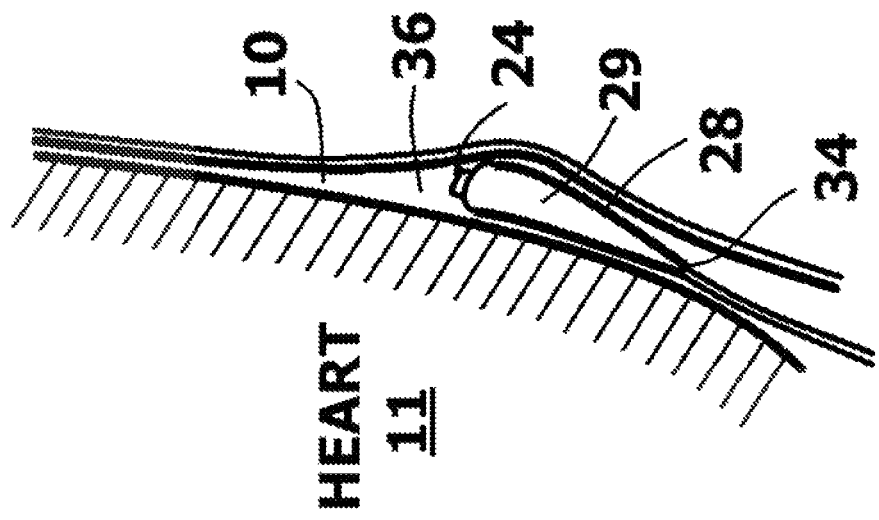
FIG. 8 shows a balloon catheter in the pericardial space in a partially expanded condition.

Referring to FIG. 8, and FIG. 9, it can be seen that each balloon catheter 29 has a leading edge 24. Suction is provided to the leading edge 24 via a suction conduit 26 that extends through the balloon catheter 29. In this manner, the balloon catheter 29 can suction away any fluid that impedes its progress as the balloon catheter 29 is advanced into the targeted area around the heart 11.

One or more expansion bladders 28 are provided on the balloon catheter 22 just behind the leading edge 24. Each expansion bladder 28 has an external wall 30 of variable thickness that causes the expansion bladder 28 to inflate in a controlled manner. The expansion bladder 28 first expands at the end that is closest to the leading edge 24. As more air is added to the expansion bladder 28, the expansion bladder 28 expands towards its second end 34. This tip-first/tail-last expansion profile creates a peristaltic action that softly drives the expansion bladder 28 forward in the direction of the leading edge 24. As the balloon catheter 29 is advanced into the pericardial cavity 10 or other tissue at that position, the expansion bladder 28 is repeatedly inflated and deflated. This action slowly and safely creates an opening 36 in the targeted area 21. As the balloon catheter 29 encounters blood, pericardial fluid and the like, the fluid is suctioned away at the leading edge 24. In this manner, using only gentle external forces, the balloon catheter 29 can create an opening 36 that is large enough to eventually host the construct.

The balloon catheters 29 are positioned around the heart 11 in targeted areas that have been previously identified as being safe for expansion. The balloon catheters 29 need not be symmetrically disposed. In this manner, areas of scar tissue and other obstructions can be avoided. Once the balloon catheters 29 are in place, the balloon catheters 29 can begin creating openings 36 in the pericardial cavity 10 or other tissue at multiple points. The openings 36 can be enlarged until they interconnect, therein creating the space required for a construct, such as the cuff of a heart pump.

Once an opening 36 of the proper size, shape and position is formed in the pericardial cavity 10 or the tissue in that area, each balloon catheter 29 is withdrawn through the delivery guide catheter 27 through which it extends. However, each delivery guide catheter 27 still provides access to the opening 36 around the heart 11 that was created. The challenge is then to insert a heart pump, or similar construct, into the opening 36 utilizing only the access provided by the delivery guide catheter 27.

Figure 10:
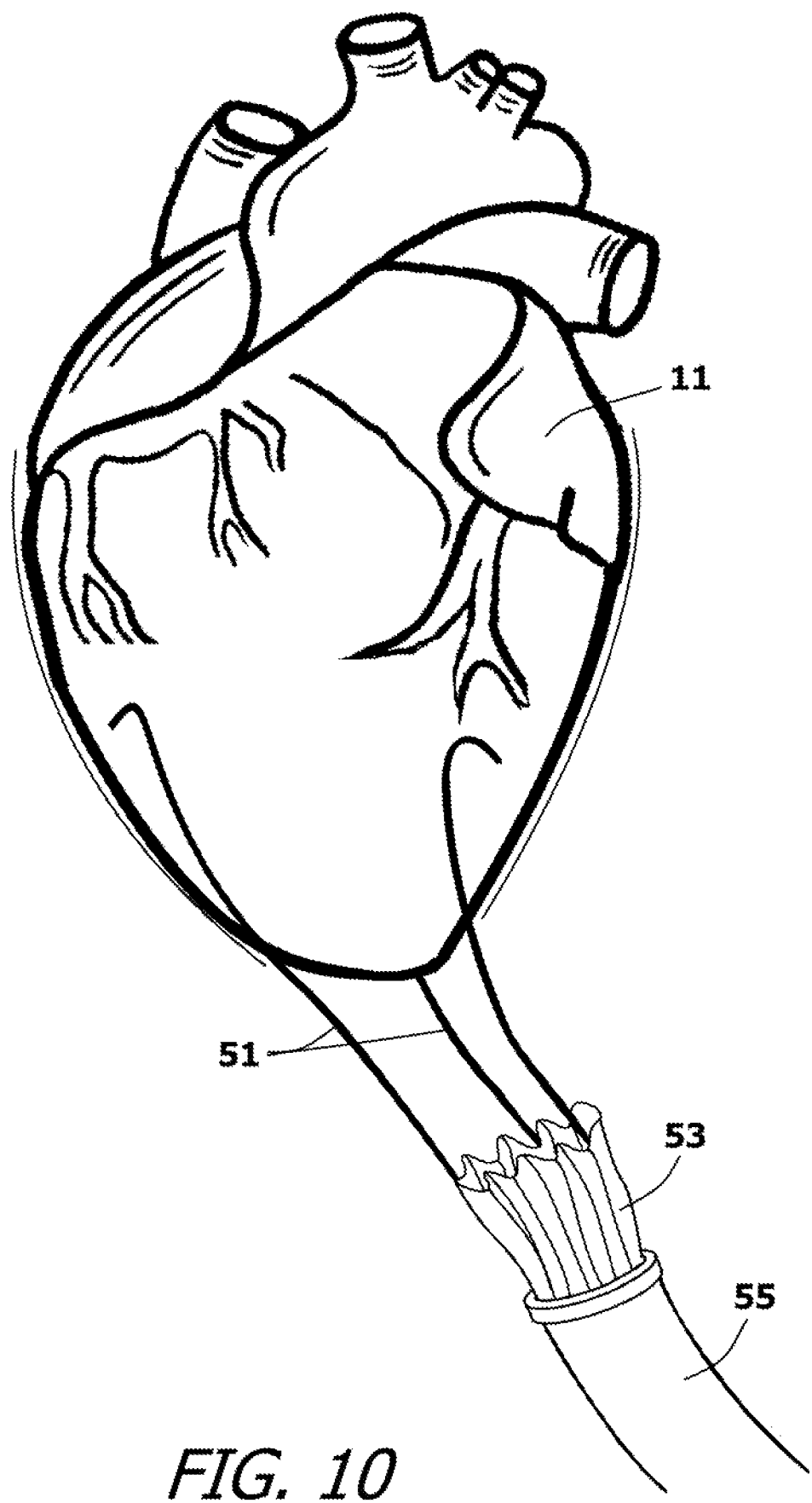
FIG. 10 shows the cuff of a heart pump construct being advanced into a prepared opening around the heart using prepositioned device deployment guides and a surgical insertion tube.

Referring to FIG. 10 in conjunction with FIG. 7, a first method of construct installation is shown. In this first method, the balloon catheters 29, if used, are removed from the delivery guide catheters 27 and are replaced with device deployment guides 51. The delivery guide catheters 27 are then removed. As such, the device deployment guides 51 are precisely positioned in the openings 36 that have been prepared. It should be understood that the balloon catheters 27 can be advanced into the pericardial area over the device deployment guides 51 rather than through the delivery guide catheters 27 previously described.

Figure 11:
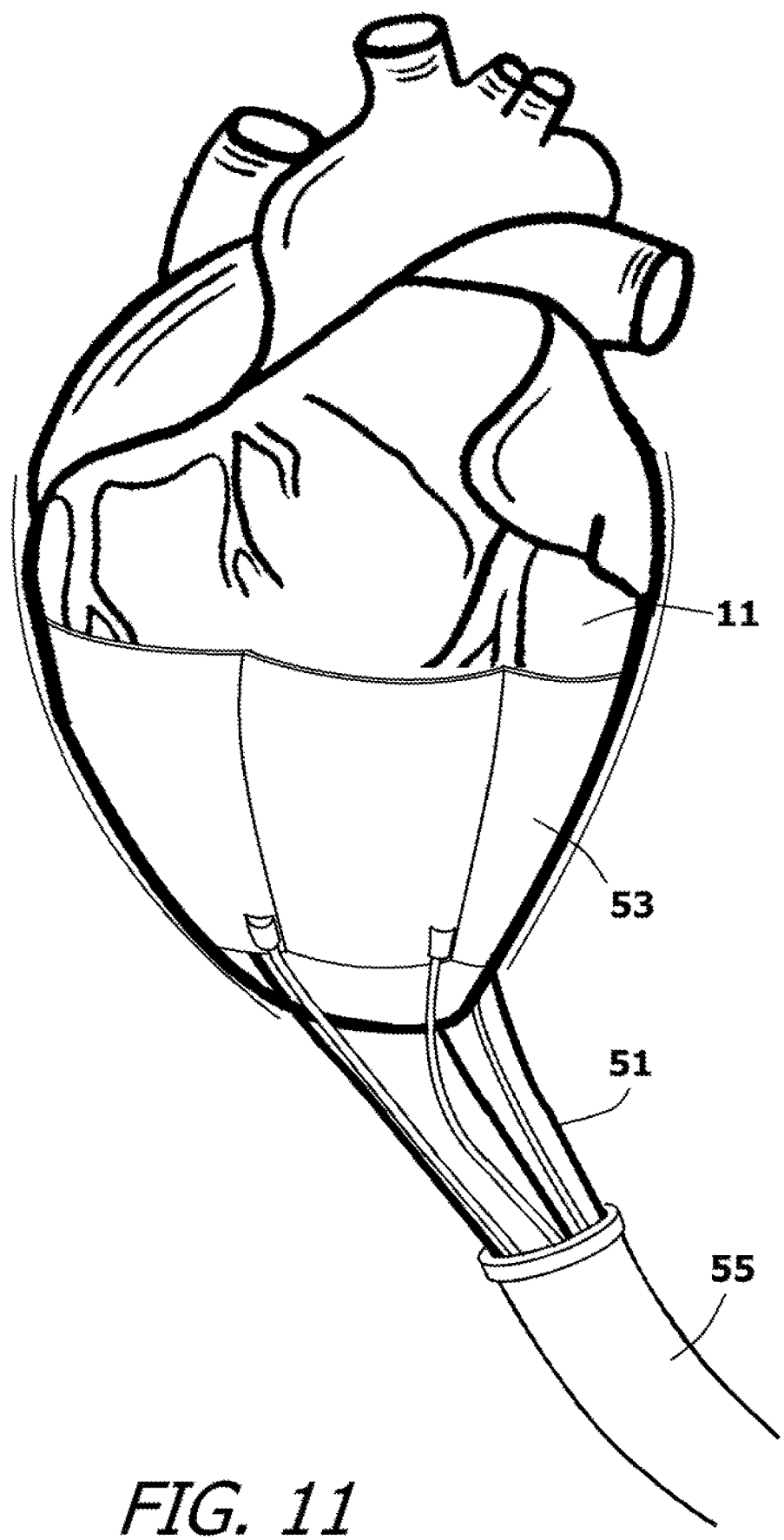
FIG. 11 shows the embodiment of FIG. 10 with the duff of the heart pump construct deployed from the surgical insertion tube.

With the device deployment guides 51 in place, a precise pathway is created to the prepared openings 36 adjacent the heart 11. The device deployment guides 51 are used to guide a construct 53 into the prepared opening 36. Furthermore, the device deployment guides 51 can be used to provide needed rigidity and resiliency to the construct 53 as is herein explained. In the shown embodiment, the construct 53 is part of a collapsible heart pump. The construct 53 engages the device deployment guides 51 and is collapsed into a surgical insertion tube 55. Referring to FIG. 11 in conjunction with FIG. 10, it can be seen that the surgical insertion tube 55 can be guided near the heart 11 using the device deployment guides 51. Once near the heart 11, construct 53 can be ejected from the surgical insertion tube 55. Once the construct 53 free is of the surgical insertion tube 55, the construct 53 expands. The expansion is created in part by the spreading of the device deployment guides 51. The construct 53 is still engaged with the device deployment guides 51 and follows the device deployment guides 51 over the heart 11. The device deployment guides 51 reinforce the construct 53 and prevent the construct 53 from collapsing away from the heart 11 both during installation and during operation. In the shown scenario of a heart pump, the device deployment guides 51 provide enough rigidity that the heart pump is capable of providing diastolic assist to the functioning of the heart 11. That is, the heart pump is rigid enough to help the heart 11 expand. This is a great improvement over prior art collapsible heart pumps that can only function to help the heart 11 contract. Accordingly, for some types of constructs 53, there is an advantage to leaving the device deployment guides 51 in place. For other constructs, the device deployment guides 51 are left in place only while the construct 53 is deployed and tested to ensure satisfactory fit and functionality. If fit and functionality can be improved, the device deployment guides 51 can be utilized to exchange a the poorly functioning construct for a construct of different type or size.

Figure 12:
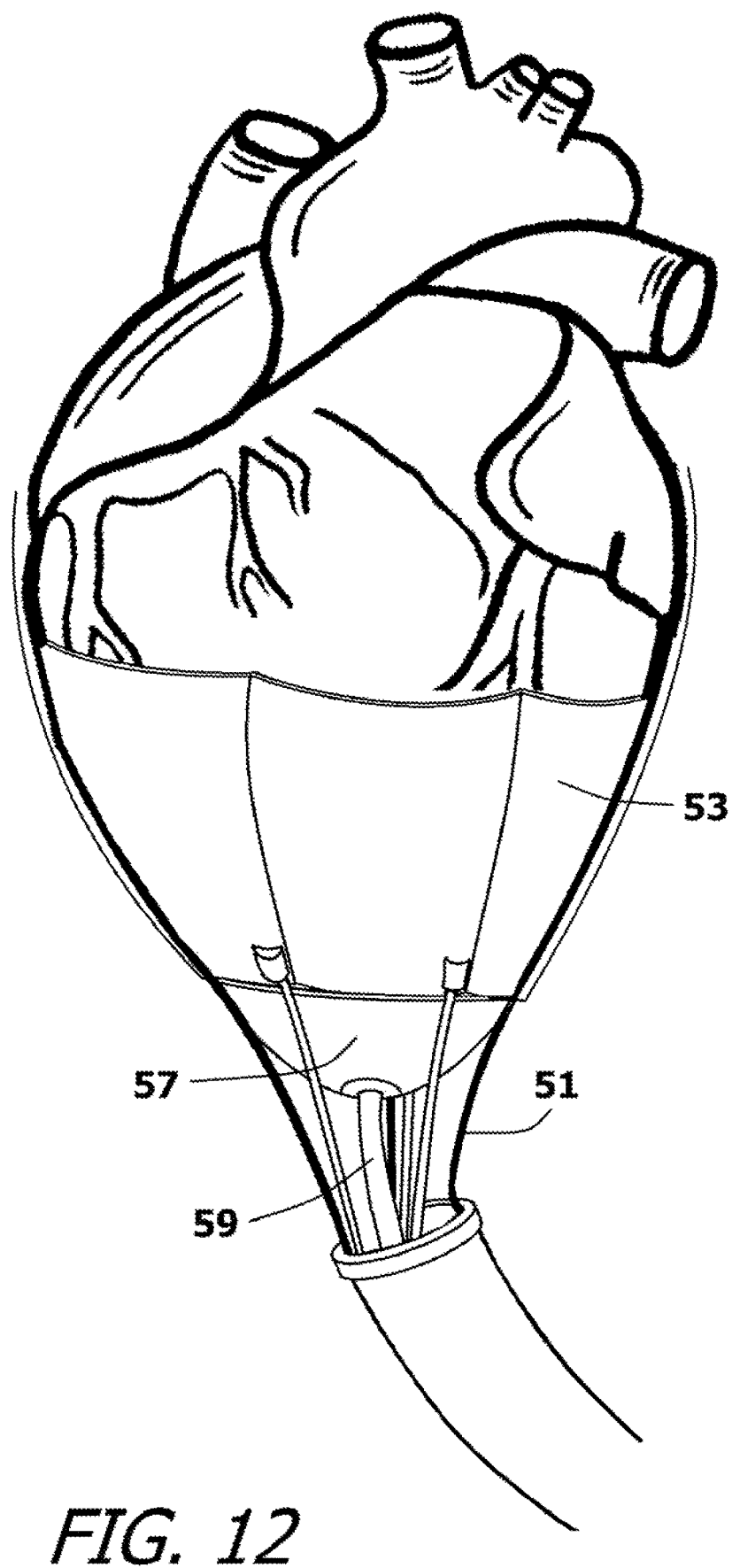
FIG. 12 shows base of the heart construct being applied to the cuff of the heart pump construct using the same guides and surgical insertion tube.

Referring to FIG. 12, it can be seen that the same device deployment guides 51 that guides the construct 53 into place can also be used to install secondary elements, such as a such end cap 57 for the heart pump that contains the pressure tubes 57 and drain tubes 59 needed for the heart pump to function.

Figure 13:
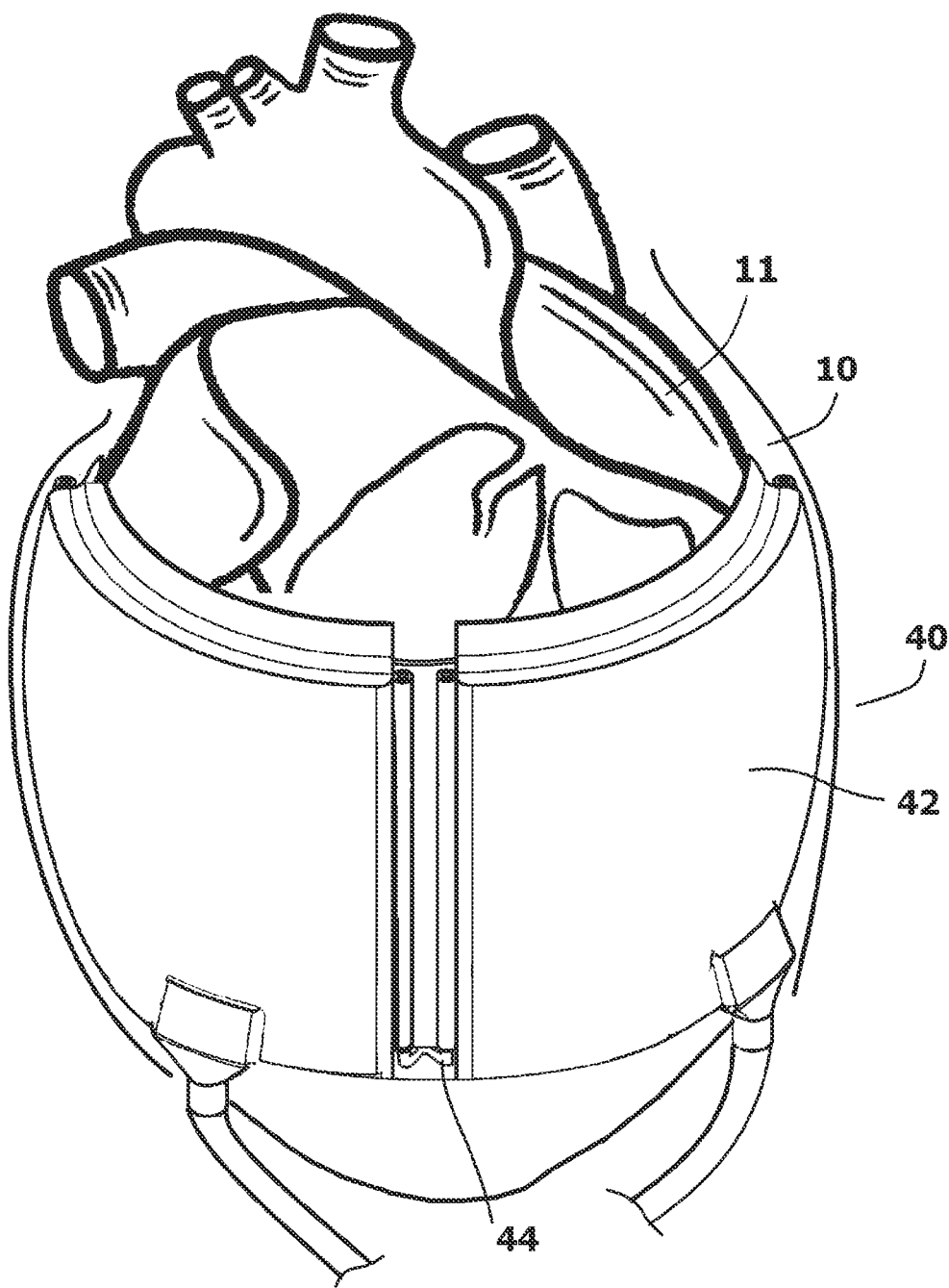
FIG. 13 shows an exemplary modular heart pump construct engaging the heart in the prepared opening.
Figure 15:
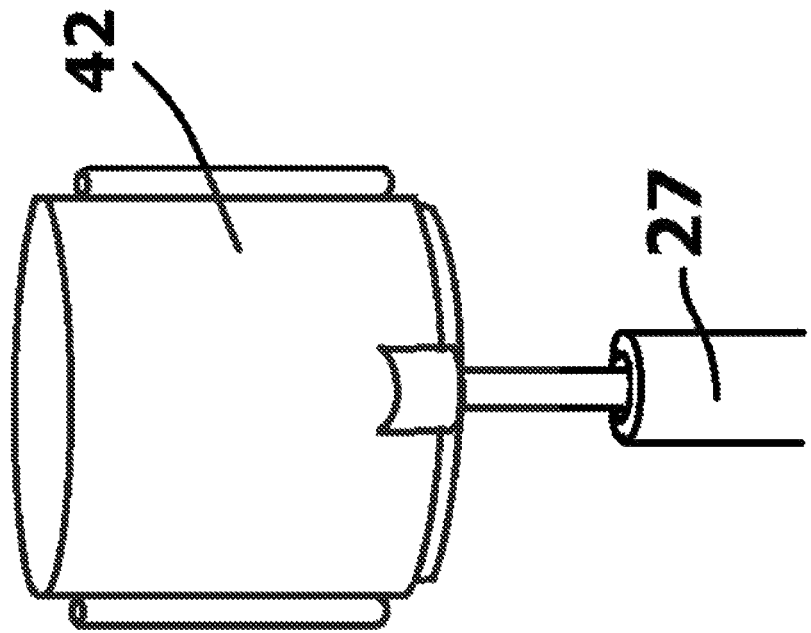
FIG. 15 shows the segment of the heart pump construct of FIG. 13 is a fully expanded condition.
Figure 14:
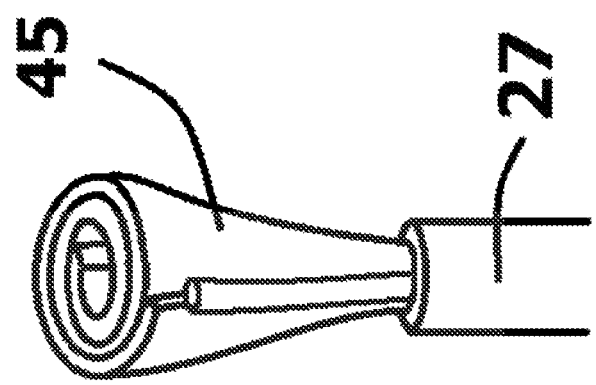
FIG. 14 shows a collapsed segment of a heart pump construct being advanced through a delivery guide catheter.

FIG. 10, FIG. 11, and FIG. 12 shows a heart pump construct 53 with a unitary cuff. Such a configuration is exemplary, and it will be understood that the cuff can be configured to only partially encircle the heart 11 or contact heart 11 only in a specific area. It will also be understood that the construct 53 can have a modular construction consisting of multiple segments that are assembled around the heart 11. Referring to FIG. 13, FIG. 14, and FIG. 15, such a modular construct is shown along with a second exemplary method of construct installation. In this embodiment, delivery guide catheters 27 are used rather than the previously described device deployment guides. A delivery guide catheter 27 is directed into the prepared opening 36 around the heart 11 in the manner previously explained. Once in position, the lumen of the delivery guide catheter 27 can be utilized to advance the construct 40 into place. The construct 40 is a modular multi-piece construct. The modular construct 40 is a heart pump with modular panels 42 that can be selectively inflated and deflated. When deflated, each modular panel 42 is pliable and can be rolled into a cylindrical shape 45 (FIG. 14). The cylindrical shape 45 is capable of being advanced through the delivery guide catheter 27 into the opening 36 that was prepared around the heart 11. Once in the prepared opening, each panel 42 can be unfurled by slightly inflating the panel 42. A heart 11 may have scar tissue, bypass anomalies or other obstacles that may prevent components of a heart pump 40 from fully encircling the ventricles of the heart 11. There are also medical scenarios where the heart's pumping function is best served by assisting only the left ventricle or the right ventricle. In both cases, the heart pump 40 can be configured to only partially encircle the heart 11.

If the heart pump 40 is intended only to act on one ventricle of the heart 11, then only one or two modular panels 42 need be advanced into the pericardial cavity 10. If the modular heart pump 40 is intended to encircle the heart 11, as is shown, then three or more modular panels 42 can be used.

If more than one modular panel 42 is inserted, then those panels 42 must be mechanically interconnected within the prepared opening 36. The interconnection is made using a linkage element 44 that can also be advanced and manipulated through the delivery guide catheter 27 or through a secondary catheter that has been advanced through a secondary incision. The modular panels 42 can be interconnected and operated in the manner described in co-pending U.S. patent application Ser. No. 18/160,963, filed Jan. 27, 2023, the disclosure of which is herein incorporated by reference.

Figure 16:
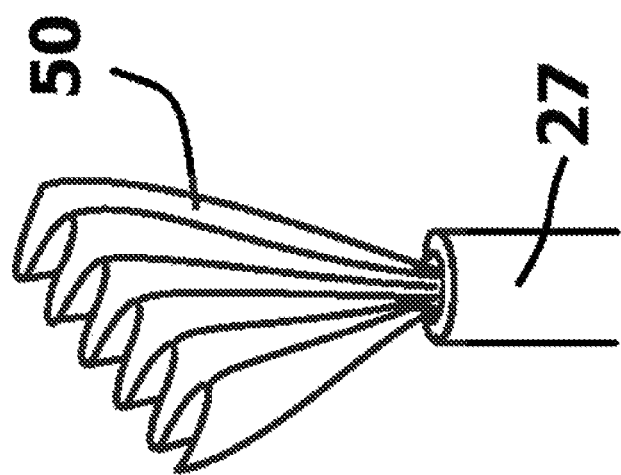
FIG. 16 shows an alternate embodiment for a segment of a heart pump construct.

Referring to FIG. 16, an alternate configuration of a modular panel 50 is shown. In this configuration, each modular panel 50 collapses with a corrugated fold 52 rather than the previously described rolled configuration. The corrugated fold 52 enables the modular panel 50 to pass through the delivery guide catheter 27.

Figure 17:
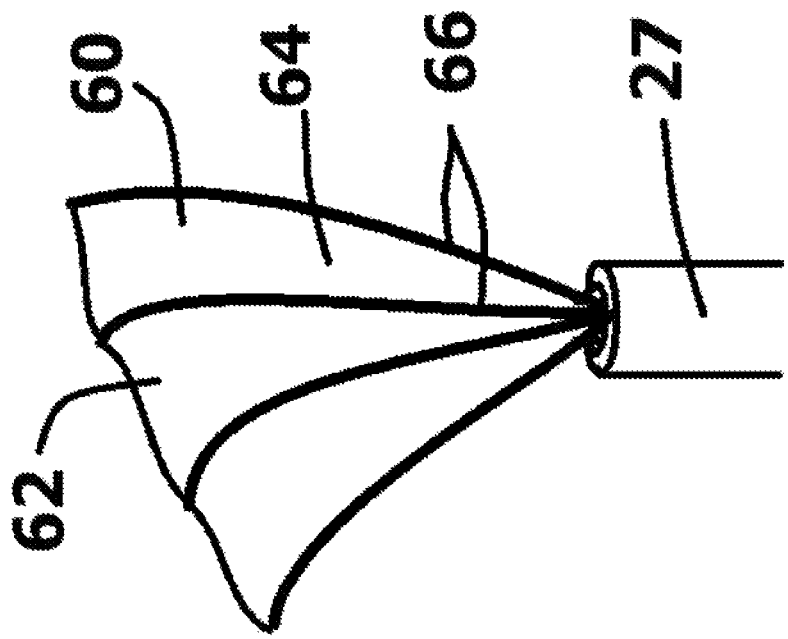
FIG. 17 shows another alternate embodiment for a segment of a heart pump construct.

Referring to FIG. 17, another alternate configuration for a modular panel 60 is shown. In this configuration, each modular panel 60 collapses with a sail fold 62 rather than the previously described rolled or corrugated configurations. Each modular panel 60 has a sail configuration, wherein a pliable bladder 64 is suspended along two or three support wires 66. The support wires 66 are biased to spread apart and open the pliable bladders 64 as the support wires 66 exit the delivery guide catheter 27.

Figure 18:
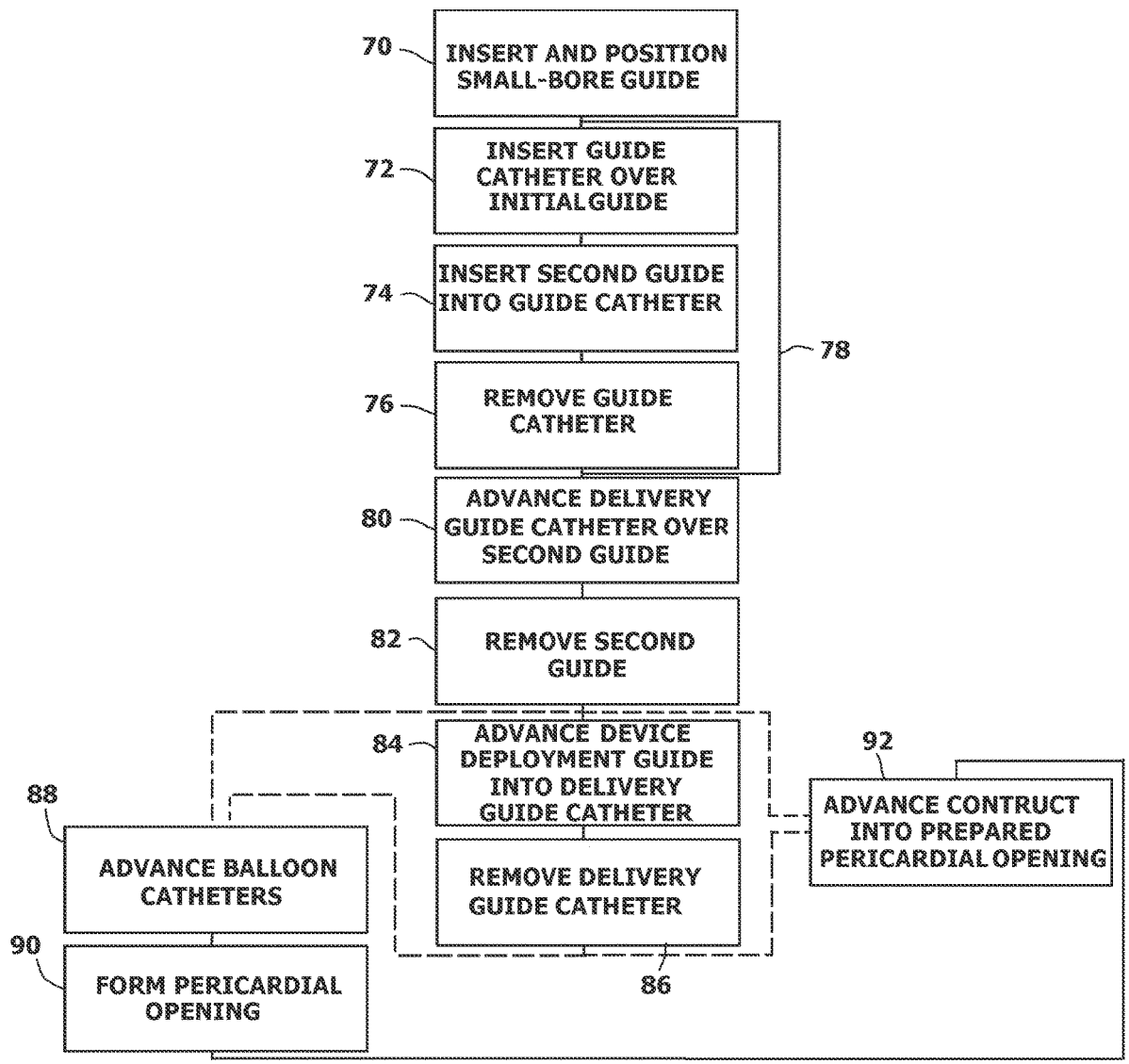
FIG. 18 is a block diagram outlining the methodology for safely forming an opening for a construct about the heart.

Referring to FIG. 18 in conjunction with all previous figures, the overall methodology is outlines for preparing an opening around the heart and properly installing a construct into that opening. To initial the method, a first small-bore guide 12 is advance toward the heart 11 and is used to probe an otherwise interrogate the areas of tissue surrounding the heart 11. See Block 70. The small-bore guide 12 is positioned where the probing of the available anatomy indicates would be best to effectively and safely insert a construct. A larger bore guide catheter 20 is then advanced into position using the first small-bore guide 12. See Block 72. The small-bore guide 12 is removed and is replaced with a stiffer second guide 25. See Block 74. The guide catheter 20 is removed, therein leaving the second guide 25. See Block 76. As is indicated by loop line 78, this process can be incrementally repeated until a guide is in place that can be used to direct a delivery guide catheter 27 into place.

A delivery guide catheter 27 is then advanced over the second guide 25. See Block 80. The second guide 25 is removed, therein leaving the delivery guide catheter 27. See Block 82.

If balloon catheters 29 are to be used, the balloon catheters 29 can be advanced through the delivery guide catheter 27 where they are used to create the opening 36 in the pericardial area. See Block 88 and Block 90. The balloon catheters 29 are then withdrawn. The surgeon now has a prepared opening 36 around the heart 11 and one or more delivery guide catheters 27 in place that lead to that opening 36. The surgeon can decide to use the delivery guide catheters 27 to advance a construct to into the opening 36. Alternatively, the surgeon can advance device deployment guides 51 into the delivery guide catheters 27. See Block 84. The delivery guide catheters 27 can then be withdrawn leaving the delivery guide catheters 27. See Block 86. A construct 53 can then be guided into place along the device deployment guides 51. See Block 92. Once the construct 53 is in the created opening 36, device deployment guides 51 need not be removed. If the construct is ineffective, the construct 53 can be replaced in the prepared opening 36 using the same delivery guide catheters 27 or device delivery guides 51.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method of positioning a construct near the heart, comprising:
    advancing a flexible first guide into a targeted area adjacent the heart;
    creating an opening in said targeted area by advancing at least one balloon catheter into said targeted area and cyclically inflating and deflating said at least one balloon catheter in a manner that generates peristaltic movement that biases said at least one balloon catheter further into said targeted area;
    using said flexible first guide to direct a larger guide catheter over said flexible first guide into said targeted area;
    using said larger guide catheter to direct a second guide into said targeted area, wherein said second guide is stiffer than said flexible first guide;
    using said second guide to direct a delivery guide catheter into said targeted area;
    using said delivery guide catheter to advance a device deployment guide into said targeted area; and
    utilizing said device deployment guide to advance said construct into said targeted area.

2. The method according to claim 1, further including preparing said targeted area to receive said construct.

3. The method according to claim 2, wherein preparing said targeted area includes probing said targeted area with said flexible first guide to determine if any obstacles to the insertion of said construct exist.

4. The method according to claim 2,
    wherein said opening in said targeted area is sized to receive said construct.

5. The method according to claim 4, wherein said at least one balloon catheter is advanced into said targeted area through said delivery guide catheter.

6. The method according to claim 4, wherein said at least one balloon catheter is advanced into said targeted area over said device delivery guide.

7. The method according to claim 1, wherein said construct is a heart pump.

8. The method according to claim 7, wherein said device deployment guide supports said heart pump while said heart pump operates in vivo, therein enabling said heart pump to assist in diastolic function.

9. The method according to claim 7, further including testing said heart pump in vivo prior to removing said device deployment guide.

10. The method according to claim 7, wherein said heart pump has interconnectable sections, wherein each of said interconnectable sections is advanced into said targeted area and are assembled into said heart pump within said targeted area.

11. A method, comprising:
    preparing a targeted area proximate a heart by advancing at least one balloon catheter into said targeted area and cyclically inflating and deflating said at least one balloon catheter as said at least one balloon catheter advances into said targeted area, wherein said at least one balloon catheter inflates in a manner that generates peristaltic movement that biases said at least one balloon catheter further into said targeted area;
    advancing at least one guide in vivo into said targeted area;
    providing a construct that can be guided by said at least one guide in vivo;
    advancing said construct along said at least one guide in vivo to said heart; and
    positioning said construct into an operable position relative said heart utilizing said at least one guide.

12. The method according to claim 11, wherein advancing said construct along said at least one guide includes advancing said construct along an exterior of said at least one guide.

13. The method according to claim 11, wherein advancing said construct along said at least one guide includes advancing said construct inside said at least one guide.

14. The method according to claim 12, wherein said guide provides structural integrity to said construct and remains engaged with said construct in vivo as said construct functions.

15. The method according to claim 11, wherein said construct is modular and has separate sections, wherein advancing said construct includes advancing said sections into said at least one position.

16. A method of positioning a construct into a targeted area near the heart, comprising:
    preparing said targeted area to receive said construct by advancing a first guide into a targeted area;
    advancing at least one balloon catheter into said targeted area along said first guide and selectively expanding said at least one balloon catheter to create an opening in said targeted area that is sized to receive said construct by cyclically inflating and deflating said at least one balloon catheter in a manner that generates peristaltic movement that biases said at least one balloon catheter further into said targeted area;
    using said at least one balloon catheter to direct a second guide into said targeted area;
    using said second guide to direct a delivery guide catheter into said targeted area;
    using said delivery guide catheter to advance a device deployment guide into said targeted area; and
    utilizing said device deployment guide to advance said construct into said targeted area.

17. The method according to claim 16, wherein said device deployment guide provides structural integrity to said construct and remains engaged with said construct in vivo as said construct functions.

* * * * *